(12) United States Patent
Doerr et al.

(10) Patent No.: US 7,983,752 B2
(45) Date of Patent: Jul. 19, 2011

(54) ANTITACHYCARDIAC STIMULATOR

(75) Inventors: Thomas Doerr, Berlin (DE); Peter Schneider, Berlin (DE); Torsten Lang, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 352 days.

(21) Appl. No.: 12/426,325

(22) Filed: Apr. 20, 2009

(65) Prior Publication Data

US 2009/0264947 A1 Oct. 22, 2009

(30) Foreign Application Priority Data

Apr. 22, 2008 (DE) .......................... 10 2008 020 022

(51) Int. Cl.
*A61N 1/362* (2006.01)

(52) U.S. Cl. .............................................. 607/14; 607/4

(58) Field of Classification Search .................. 607/4, 5, 607/9, 14, 15, 28
See application file for complete search history.

(56) References Cited

U.S. PATENT DOCUMENTS

| | | | |
|---|---|---|---|
| 5,686,793 A | 11/1997 | Turner et al. | |
| 5,891,170 A | 4/1999 | Nitzsche et al. | |
| 6,748,269 B2 | 6/2004 | Thompson et al. | |
| 6,889,080 B2 | 5/2005 | Henry et al. | |
| 6,978,177 B1 | 12/2005 | Chen et al. | |
| 7,149,577 B2 | 12/2006 | Sharma et al. | |
| 7,174,209 B2 | 2/2007 | Thompson et al. | |
| 2004/0093037 A1 | 5/2004 | Henry | |

OTHER PUBLICATIONS

German Search Report for priority application, dated Mar. 12, 2009.

*Primary Examiner* — Brian T Gedeon
(74) *Attorney, Agent, or Firm* — ARC IP Law, PC; Joseph J. Mayo (57) ABSTRACT

Implantable cardiac stimulator, with chamber stimulation unit connectable to left/right ventricular stimulation electrode to generate/deliver chamber stimulation pulses for stimulation of ventricle; ventricular sensing unit (VSU) to detect respective chamber contraction and deliver ventricular sensing signal when chamber contraction detected; optional atrial stimulation unit, connectable to atrial stimulation electrode to generate atrial stimulation pulses to stimulate atrium; atrial sensing unit, to detect atrial contraction, deliver atrial sensing signal indicating respective atrial event; tachycardia detection unit, connected to VSU to detect and categorize ventricular/supraventricular tachycardia; treatment control unit (TCU), triggers chamber stimulation unit to deliver antitachycardiac stimulation (ATP); analyzer unit, connected to atrial sensing unit and TCU. Analyzes atrial events from sensing unit before/during/after delivering antitachycardiac stimulation for atrial rhythm pattern during ventricular ATP by comparison atrial rhythm pattern immediately before ATP and to trigger TCU as function of ATP response signal representing comparison result for selection of the following antitachycardiac treatment.

15 Claims, 6 Drawing Sheets

ANTITACHYCARDIAC STIMULATOR

This application takes priority from German Patent Application DE 10 2008 020 022.0, filed 22 Apr. 2008, the specification of which is hereby incorporated herein by reference.

BACKGROUND OF THE INVENTION

1. Field of the Invention

The invention relates to an implantable cardiac stimulator for treatment of tachycardiac arrhythmias. Such a cardiac stimulator is also known as an implantable cardioverter/defibrillator (ICD) and usually also fulfills the function of an implantable cardiac pacemaker.

2. Description of the Related Art

The implantable cardiac stimulator discussed herein comprises:
- a chamber stimulation unit, which is connected or connectable to a left ventricular or right ventricular stimulation electrode and is designed to generate and deliver chamber stimulation pulses for stimulation of a ventricle of a heart,
- a ventricular sensing unit, which is designed to detect a respective chamber contraction and to deliver a ventricular sensing signal in the case of a detected chamber contraction,
- an atrial sensing unit, which is designed to detect an atrial contraction, and in the case when an atrial contraction is detected, to deliver a respective atrial sensing signal indicating a respective atrial event,
- a tachycardia detection unit which is connected to at least one ventricular sensing unit and is designed to detect a tachycardia and to categorize it as a ventricular tachycardia (VT) or as a supraventricular tachycardia (SVT), and
- a treatment control unit, which is designed to control at least the chamber stimulation unit for delivering antitachycardiac stimulation (ATP).

Stimulation and sensing electrodes may be identical to one another and may alternately serve to deliver stimulation pulses and receive myocardial potentials.

Tachyarrhythmia is understood to be an arrhythmia which leads to a heart rate higher than is physiologically appropriate. A distinction is made between tachycardia and fibrillations. In tachycardia (cardiac flutter), there is still a contraction of the affected chamber of the heart, but fibrillation is characterized in that the affected chamber of the heart is exposed to a recurring stimulation in which parts of the myocardium of the heart chamber are relaxing already while other parts are just beginning to contract, so there is no periodic contraction and relaxation of the heart chamber with the volume change that is required for pumping. Of the tachycardias, a distinction is made between ventricular tachycardias (VT) and supraventricular tachycardias (SVT), which are tachyarrhythmias of one or both heart chamber (right and/or left ventricles). Whereas supraventricular tachycardias have their origin in the atrium and are conducted to the respective ventricle by atrioventricular stimulus conduction, ventricular tachycardias have their origin in the respective ventricle itself.

Currently all manufacturers of implantable cardioverter defibrillators (ICDs) offer devices capable of discriminating between ventricular (VT) and supraventricular tachycardia therapy (SVT). One thing these instruments all have in common is that they ascertain the origin of the tachyarrhythmia before treating any tachyarrhythmia and, depending on its origin, initiate a corresponding treatment.

However, known approaches for differentiating between ventricular and supraventricular tachycardia consist of classifying irregular rapid atrial and ventricular rhythms as VT, for example, and classifying regular rapid rhythms as SVT; see, for example, U.S. Pat. No. 5,686,793, U.S. Pat. No. 5,891,170, U.S. Pat. No. 6,748,269, U.S. Pat. No. 6,889,080, U.S. Pat. No. 7,174,209 and US 2004/0093037. It is possible in this way to discriminate between VT and SVT even before initiating a corresponding therapy.

None of the instruments available currently has 100% specificity, i.e., this results in inadequate delivery of treatment. In this context, painful delivery of shocks should be regarded as especially critical because they would drastically lower acceptance of ICD therapy.

So-called "active" discrimination algorithms capable of improving the discrimination result by means of targeted ventricular or atrial stimulation and observation of the next respective chamber (atrium or ventricle) have not become established. The main disadvantage here is the delay in the detection decision associated with the stimulation phase and the proarrhythmic potential of such stimulation prior to the detection decision.

BRIEF SUMMARY OF THE INVENTION

The object of the present invention is to prevent inadequate shock therapies in the case of arrhythmias that are attributed to a ventricular tachycardia, i.e., they fall in a predefined VT zone. However, a necessary (adequate) ventricular therapy should not be additionally delayed in comparison with the current algorithms, if possible.

According to the present invention, the object is achieved by an implantable cardiac stimulator of the aforementioned type, which additionally has an analyzer unit that is connected to the atrial sensing unit and to the treatment control unit and is designed to analyze atrial events detected by the sensing unit before, during and after delivery of an antitachycardiac stimulation (ATP), comparing them with regard to the atrial rhythm pattern during ventricular ATP with the atrial rhythm pattern immediately before ATP and triggering the treatment control unit as a function of the result of the comparison for selection of the subsequent antitachycardiac treatment.

U.S. Pat. No. 7,149,577 discloses a similar concept, but is not based on analysis of atrial rhythm patterns. U.S. Pat. No. 7,149,577 describes the analysis of the rhythm before and after stimulation in the channel in which the stimulation itself takes place. In contrast with that, the rhythm is fundamentally analyzed here in a different channel than in the channel stimulated (specifically in the atrium in ventricular ATP). Furthermore, it is now possible to perform the rhythm analysis even during stimulation. This is ruled out in principle in U.S. Pat. No. 7,149,577.

The underlying hypothesis is that with a fast rhythm in the atrium and ventricle at the same time, in SVT the rhythm pattern of the atrial rhythm is not influenced by the ventricular stimulation, but in "true" VT, it is modulated by the ventricular stimulation. However, the current algorithms for VT/SVT discrimination do not differentiate according to the following treatment (ATP painless/shock painful) and also do not take the information that is available during the delivery of the treatment into account in the treatment decision. The analyzer unit is thus a type of second tachycardia discrimination unit.

In summary, the invention thus comprises:
a) an implantable antitachycardiac stimulator, having at least one stimulation and detection electrode in the right ventricle of the heart (RV) or in the left ventricle (LV and/or CS) and at least one electrode for detecting the atrial signal (RA or LA) and at least one defibrillation shock electrode, b) having a device for detecting ventricular and atrial events,
c) having a device for initial detection of VT including discrimination of VT and SVT (may also be a single chamber),
d) having a device for delivering at least one ventricular ATP,
e) having a device for detection of atrial events immediately before and during ventricular ATP,
f) having an analyzer unit for comparison of the atrial rhythm pattern during ventricular ATP with the atrial rhythm pattern immediately before ATP and
g) having a treatment control unit which selects the subsequent antitachycardiac treatment as a function of the result of (f).

The cardiac stimulator is preferably an antitachycardiac stimulator having at least one VT zone and one VF zone, i.e., tachycardiac heart rates up to a limit rate, which represents an upper limit of the VT zone, are classified as a tachycardia, and heart rates above this limit rate, which also represents a lower limit of the VF zone, are classified as ventricular fibrillation. The term "zone" also refers to ranges of heart rates, which are classified as tachycardia in the case of the VT zone and as fibrillation in the case of the VF zone. The concept of different zones is essentially known to one skilled in the art, e.g., from U.S. Pat. No. 5,144,947 or US 2004/0093037.

In addition, the cardiac stimulator is preferably an antitachycardiac stimulator having a device for delivering at least one defibrillation shock, i.e., with a defibrillation shock generator, which is connected or connectable to a defibrillation shock electrode and is designed to generate and deliver a defibrillation shock for defibrillation of at least one heart chamber.

The treatment control unit here may be designed to inhibit a defibrillation shock as a function of the ATP response signal, preferably only when the ventricular heart rate is in a VT zone but not in a VF zone.

The analyzer unit may be designed to evaluate the atrial rhythm immediately after an ATP and in comparison with the atrial rhythm immediately before the ATP.

The following additional variants of a treatment sequence control by the treatment control unit are advantageous:
depending on the ATP response signal, the following antitachycardiac treatment is inhibited.
depending on the ATP response signal, the following antitachycardiac treatment is continued.
depending on the ATP response signal, the following antitachycardiac ventricular therapy is replaced by an atrial antitachycardiac therapy.
depending on the ATP response signal, first a new VT/SVT classification (tachycardia discrimination) is initiated.
depending on the ATP response signal, the parameters of the ventricular antitachycardiac therapy (ATP) are adapted.

The inventive approach offers the advantage that the specificity of the VT/SVT discrimination can be further increased and thus the number of inadequate shock therapies is reduced. This reduction leads to increased acceptance of ICD therapy. This improvement in discrimination does not result in any lengthening of the detection time for VT detection.

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
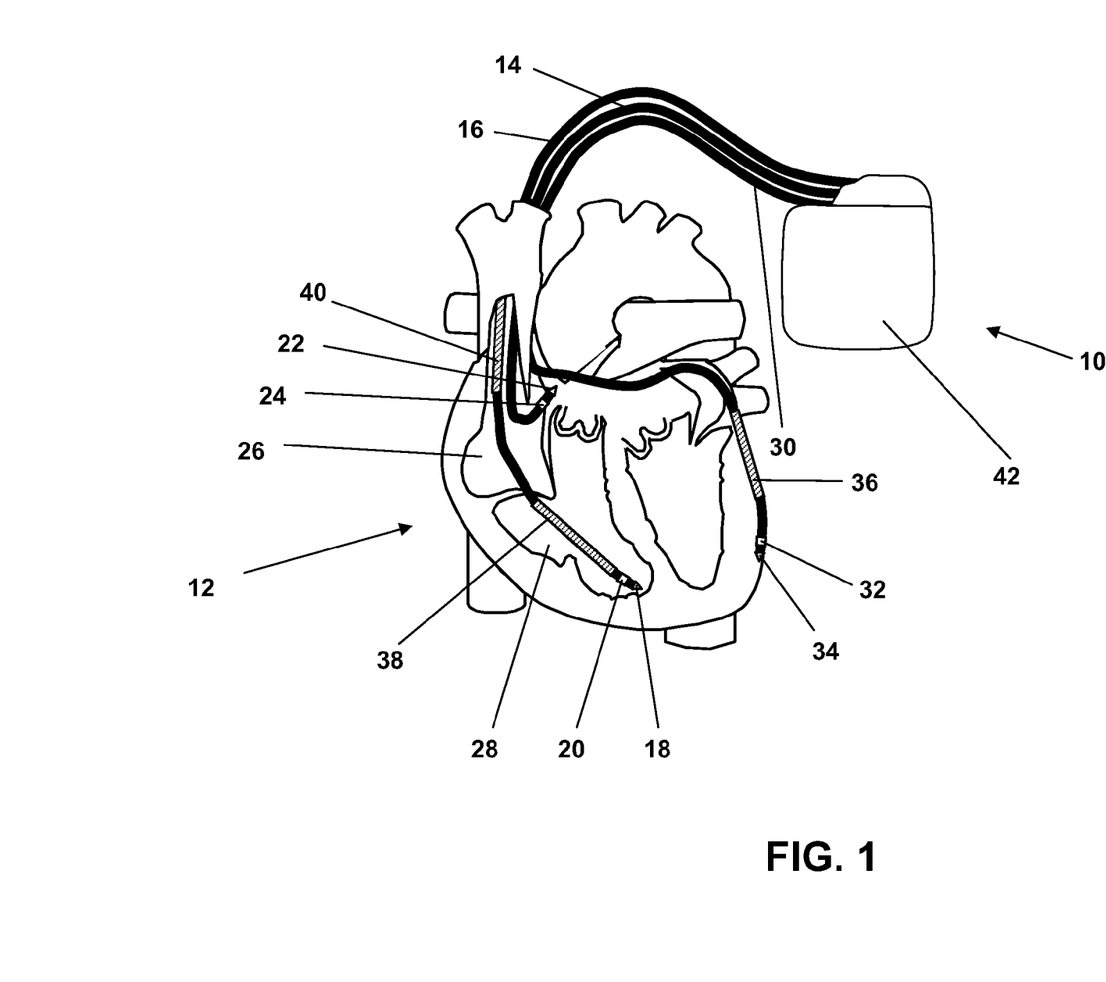
FIG. 1: shows an implantable three-chamber cardioverter/defibrillator as an example of a cardiac stimulator in combination with electrode lines connected thereto.

FIG. 1 shows an implant 10 in the form of a biventricular three-chamber heart pacemaker and cardioverter/defibrillator (ICD). Three electrode lines are connected to it, namely a right atrial electrode line 14, a right ventricular electrode 16 and a left ventricular electrode line 30. In the implanted state, the right atrial electrode line 14 ends in the right atrium 26 of the heart 12. The right ventricular electrode line 16 ends in the right ventricle 28 of the heart 12 and the left ventricular electrode line 30 extends over the coronary sinus of the heart 12 up to the left ventricle of the heart.

The right atrial electrode line 14 has on its distal end a right atrial tip electrode 22, and at a slight distance therefrom, a right atrial ring electrode 24. Similarly, the right ventricular electrode line 16 has a right ventricular tip electrode 18 on its distal end, and at a slight distance therefrom, a right ventricular ring electrode 20. A left ventricular tip electrode 34 is attached to the distal end of the left ventricular electrode line 30, and at a slight distance therefrom, a left ventricular ring electrode 32 is also attached there. These electrodes serve to receive electric potentials in the respective chamber of the heart and to deliver stimulation pulses to the respective chamber of the heart in normal pacemaker operation.

The right ventricular electrode line 16 also has a right ventricular shock coil 38 arranged in the right ventricle in the implanted state as a defibrillation electrode and a second shock coil 40 implanted in the superior vena cava. A left ventricular shock coil 36 is also attached to the left ventricular electrode 30. The shock coils serve as defibrillation electrodes to deliver defibrillation shocks if needed.

Figure 2:
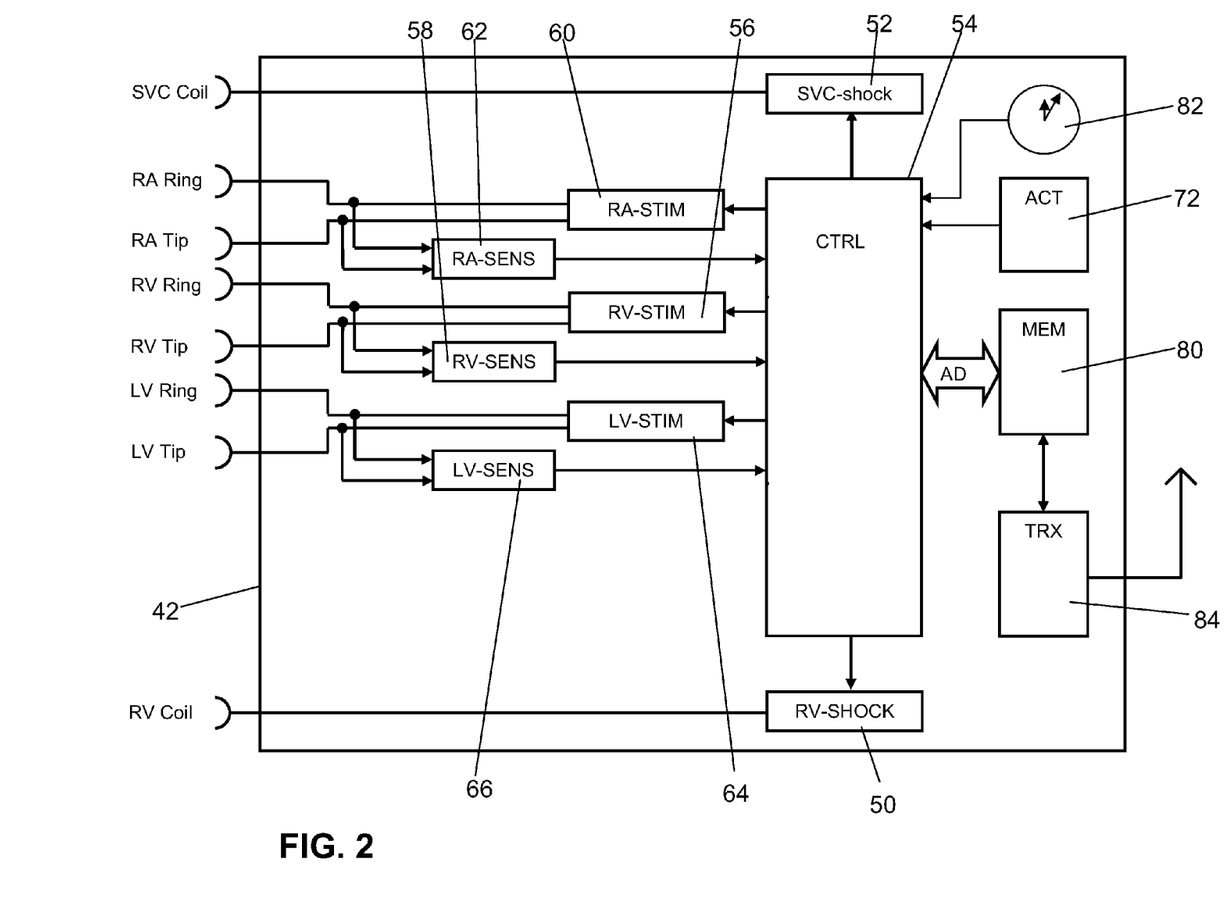
FIG. 2: shows a schematic block diagram of the cardiac stimulator from FIG. 1.

FIG. 2 shows the main components of the cardiac stimulator 10. The electric terminals for the various electrodes 18, 20, 24, 22, 32, 34, 36, 38 and 40 are shown on the left side. The shock electrodes 38 and 40 as well as 36 are each connected to a right ventricular shock pulse generator 50 and/or SVC shock generator 52. Both shock generators 50 and 52 are connected to a stimulation control unit 54, which triggers the two shock pulse generators 50 and 52 as needed to generate and deliver a defibrillation shock.

The terminal for the right ventricular tip electrode RV tip and the terminal for the right ventricular ring electrode RV ring are each connected to a right ventricular stimulation unit 56 and a right ventricular sensing unit 58. Both the right ventricular stimulation unit 56 and the right ventricular sensing unit 58 are connected to the stimulation control unit 54.

The right ventricular stimulation unit 56 is designed to generate a right ventricular stimulation pulse in response to a trigger signal of the stimulation control unit 54 and to deliver the pulse at the terminal for the right ventricular ring electrode RV ring and the right ventricular tip electrode RV tip. Alternatively it is also possible for the housing 42 of the cardiac stimulator 10 to form a neutral electrode and for the right ventricular stimulation unit 56 to be connected to the terminal for the right ventricular ring electrode RV tip and the housing 42 as another electrode for delivering a stimulation pulse. A right ventricular stimulation pulse differs from a defibrillation shock in that the stimulation pulse has a much lower pulse intensity, so that it does not stimulate the entire myocardium of a heart chamber all at once, as a defibrillation shock would, but instead stimulates only the myocardial cells in the immediate vicinity of the right ventricular tip electrode RV tip 18. This stimulus is then propagated by natural stimulus conduction over the entire right ventricle 28, thus ensuring a stimulated contraction of the right ventricle 28.

The right ventricular sensing unit 58 is designed to amplify and filter electric potentials applied to the terminal for the right ventricular ring electrode RV ring and the right ventricular tip electrode RV tip first through an input amplifier. In addition, the right ventricular sensing unit 58 is designed to analyze the course of the electric signals applied at their inputs, so that the right ventricular sensing unit 58 automatically detects a natural (intrinsic), i.e., automatic contraction of the right ventricle 28. This may be accomplished, for example, by comparing the course of the signal applied to the inputs of the right ventricular sensing unit 58 with a threshold value. The greatest amplitude of the signal in the form of the so-called R wave is typically characteristic of a natural contraction of the right ventricle 28, which can be detected by a threshold value comparison. The right ventricular sensing unit 58 then delivers a corresponding output signal, indicating a natural contraction of the right ventricle 28, to the stimulation control unit 54.

Similarly, the terminal for the right atrial tip electrode RA tip and the terminal for the right atrial ring electrode RA ring are connected to both a right atrial stimulation unit 60 and a right atrial sensing unit 62, each of which is in turn connected to the stimulation control unit 54. The right atrial stimulation unit 60 is designed to generate stimulation pulses, the intensity of which is sufficient to stimulate the right atrial myocardium. The right atrial stimulation pulses may have a different pulse intensity than the right ventricular stimulation pulses. The right atrial sensing unit 62 is designed to detect a so-called P wave, indicating a natural (intrinsic) contraction of the right atrium 26, from the course of the differential signal applied to its inputs. If the right atrial sensing unit 62 detects a corresponding P wave, it generates an output signal and delivers it to the stimulation control unit 54, characterizing a natural contraction of the right atrium 26.

In the same way, the terminal for the left ventricular tip electrode LV tip and the terminal for the left ventricular ring electrode LV ring are each connected to a left ventricular stimulation unit 64 and a left ventricular sensing unit 66. The left ventricular stimulation unit 64 and the left ventricular sensing unit 66 are also connected to the stimulation control unit 54. Both units function like the stimulation units 56 and 60 and the sensing units 58 and 62 already described.

An acceleration sensor 72 is connected to the stimulation control unit 54 as another component of the cardiac stimulator 10 and is integrated into the housing 42 of the cardiac stimulator 10. The acceleration sensor 72 is designed to detect a movement signal, depending on the patient's physical activity and to deliver a corresponding first accelerometer output signal indicating the patient's physical activity to the stimulation control unit 54. This makes it possible for the stimulation control unit 54 to adapt the timing of the stimulation pulses to the needs of the patient (hemodynamic demand).

In addition, the cardiac stimulator 10 comprises a memory unit 80, which is connected to the stimulation control unit 54 and makes it possible to save signals generated or analyzed by the stimulation control unit 54. On the other hand, the memory unit 80 makes it possible to save control programs for the stimulation control unit 54 in a variable form. Furthermore, the stimulation control unit 54 is connected to a timer 82.

The memory unit 80 is connected to a telemetry unit 84 which makes it possible to transmit data stored in the memory unit 80 to an external device wirelessly or to transmit programming commands on the part of the external device to the cardiac stimulator 10 and to save them in the memory unit 80.

Figure 3:
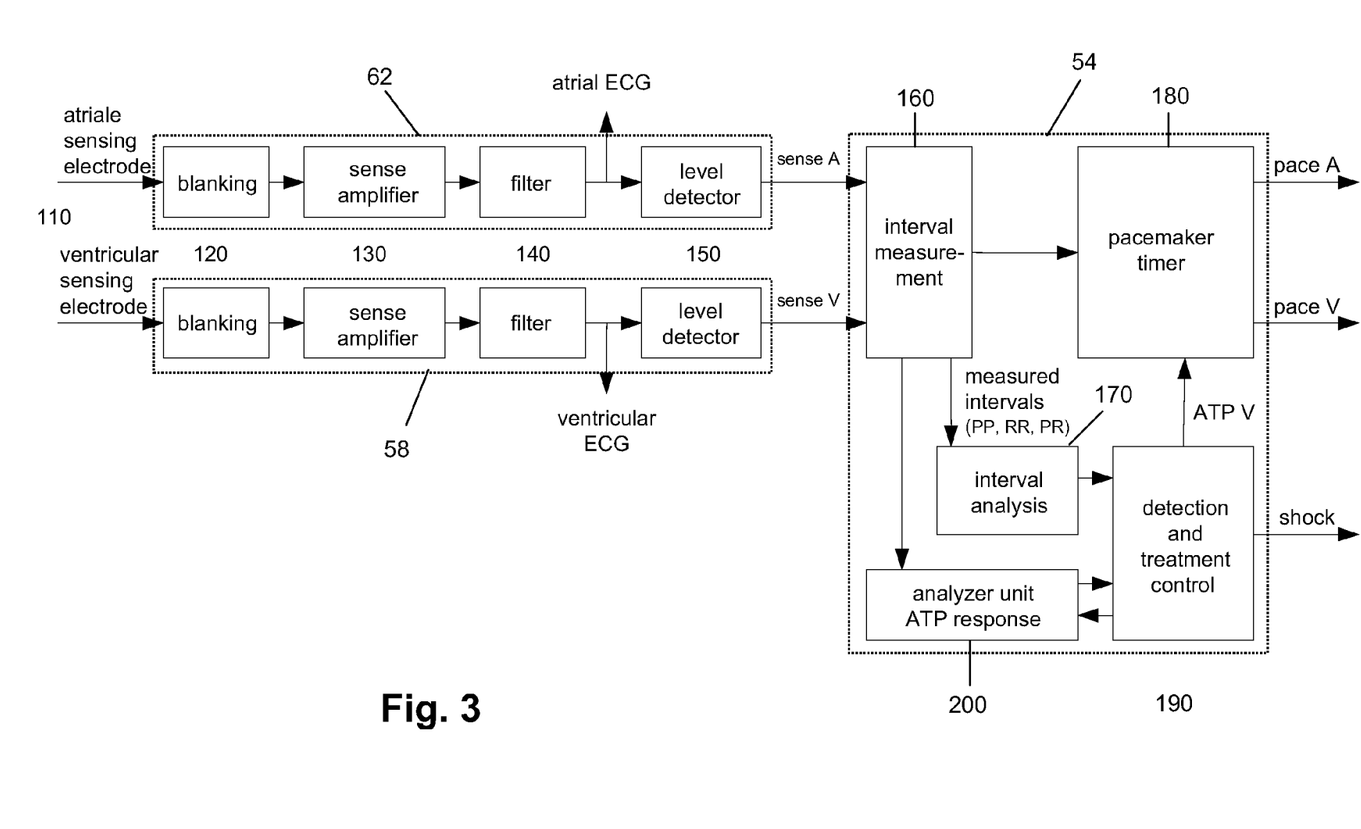
FIG. 3: shows a few components of the cardiac stimulator in a detailed diagram.

FIG. 3 shows the components of the cardiac stimulator 10 that are relevant for the invention, namely the right atrial sensing unit 62, the right ventricular sensing unit 58 and the stimulation control unit 54 in a detailed diagram, whereby this unit, in particular the stimulation control unit 54, has or may have components other than those shown in FIG. 3. The right atrial sensing unit 62 and the right ventricular sensing unit 54 are each connected to a terminal 110 for an atrial electrode and a ventricular electrode, and each has a blanking stage 120 and each has an amplifier 130, each being connected in series with one another and downstream from the respective electrode terminal 110. The respective blanking stage 120 serves to blank out stimulation artifacts in a known manner after delivering a stimulation pulse. By means of the respective amplifier 130, the intracardiac signals derived by means of the atrial and/or ventricular electrode are first amplified. The respective amplifier 130 is followed by an A/D converter and filter stage 140, which digitizes and filters the signal. The A/D converter and filter stage is followed by a comparator 150, which compares the digitized and filtered signal with a threshold value in order to detect P waves by threshold value comparison in the case of the intra-atrial signal and to detect R waves by threshold value comparison in the case of the intraventricular signal. In this way, the right atrial sensing unit 62 and the right ventricular sensing unit 58 are each capable of generating a right atrial and/or right ventricular sensing signal if there is a contraction of the respective heart chamber.

The P waves and R waves obtained from synchronous events (sensing signals) in this way are sent to the stimulation control unit 54, where they are analyzed by an interval measuring unit 160 with regard to the intervals occurring between them. The PP, PR, RP and RR intervals obtained in this way are sent to a pacemaker timer 180 for control of the antibradycardiac stimulation. Furthermore, this interval information is compared in an interval analyzer unit 170 for discrimination between VT and SVT with regard to their conditions with respect to the atrial and ventricular rhythms and this information is made available in an evaluated form to a detection and treatment control unit 190 for antitachycardiac therapy (ATP, shock).

According to the invention, the cardiac stimulator additionally has an analyzer unit 200, e.g., as a component of the stimulation control unit 54 for tachycardia discrimination, which is connected to the interval measuring unit 160 and the detection and treatment control unit 190 and is designed to generate an ATP response signal.

The analyzer unit 200 therefore analyzes the intervals determined in the interval measuring unit 160 immediately before and during an ATP. For this purpose, there is a bidirectional link between the analyzer unit 200 and the treatment control unit 190. The analyzer unit 200 is informed about the imminent ATP delivery by the treatment control unit 190 and in turn influences the treatment control unit 190 with the ATP response signal thereby obtained. The ATP response signal is determined by an interval or pattern comparison of the atrial intervals before and during a ventricular ATP. If the atrial rhythm remains unaffected by the ventricular ATP (=), then SVT is assumed. If the atrial rhythm is modulated (≠) by the ventricular ATP, then a VT is confirmed. This evaluation is designed so that the atrial intervals are replaced by interpolation, optionally being blanked out by a cross-blank during ventricular ATP.

In the following illustrations, possible sequences for the treatment sequence control by the treatment control unit 190 are shown as a function of the ATP response signal.

Figure 4:
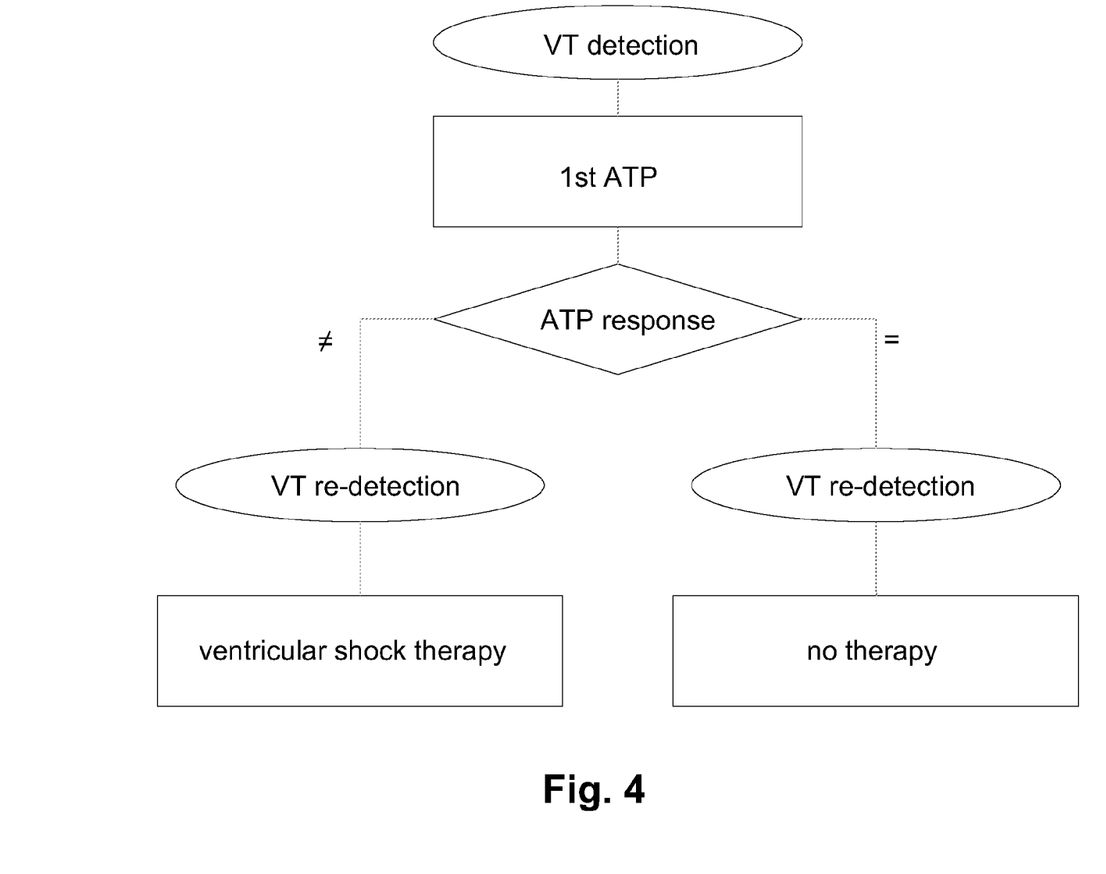
FIG. 4: shows a first implementation of a treatment control in response to an ATP response signal in the form of a flow chart.

FIG. 4 shows a simple expansion of the treatment sequence control by means of the ATP response signal. After a VT detection (with a rhythm with the atrium at the same rate) has been fulfilled, first the programmed antitachycardiac stimulation is delivered and at the same time the ATP response signal is determined. If the atrial rhythm is modulated by the ventricular ATP, then a programmed ventricular shock therapy follows ATP after VT re-detection has been performed; otherwise, despite the fact that re-detection has occurred, shock therapy is not enabled because in this case, based on the ATP response signal, the initial VT classification has been corrected in favor of SVT.

Figure 5:
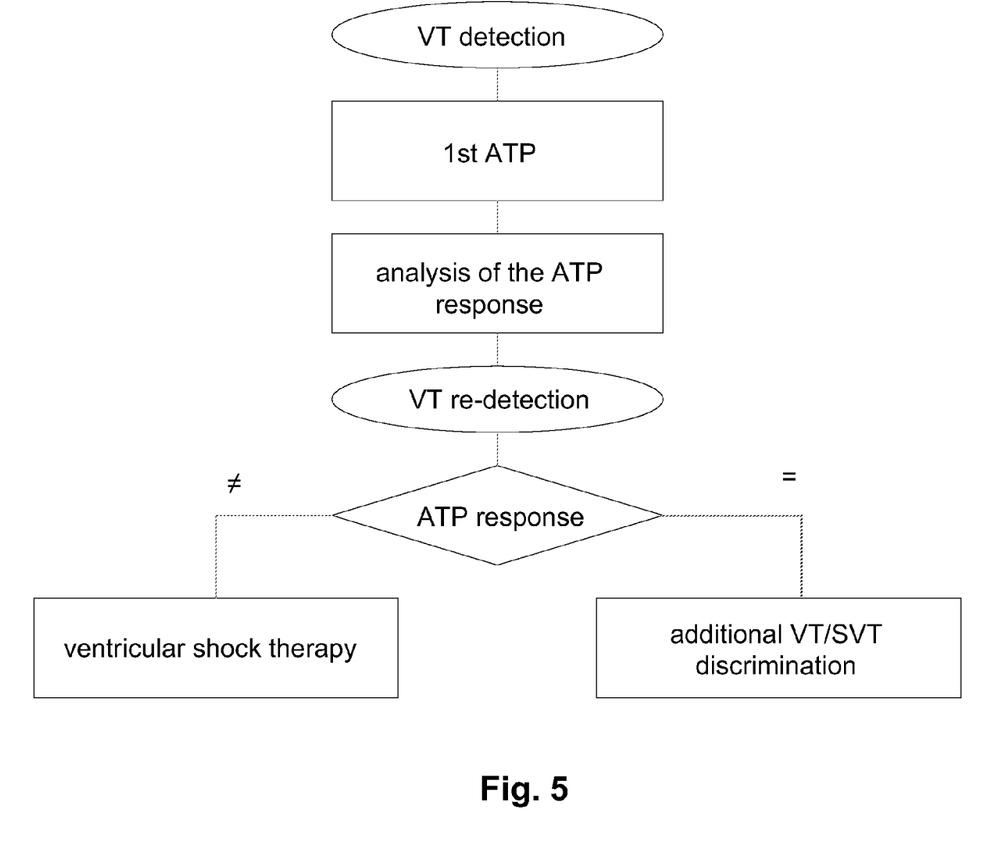
FIG. 5: shows a second implementation of a treatment control in response to an ATP response signal in the form of a flow chart.

An alternative implementation is illustrated in FIG. 5, where ATP occurs after an initial VT detection and there is a simultaneous analysis of the ATP response signal. If a renewed VT re-detection occurs after ATP, then depending on the ATP response signal, either a ventricular shock therapy is delivered or the VT/SVT discrimination is started again. It is thus possible to ensure a short re-detection time between ATP and shock therapy and to initiate a lengthened re-detection with expanded discrimination criteria (e.g., prolonged detection counter) only in the case of "doubtful" VT classification.

Figure 6:
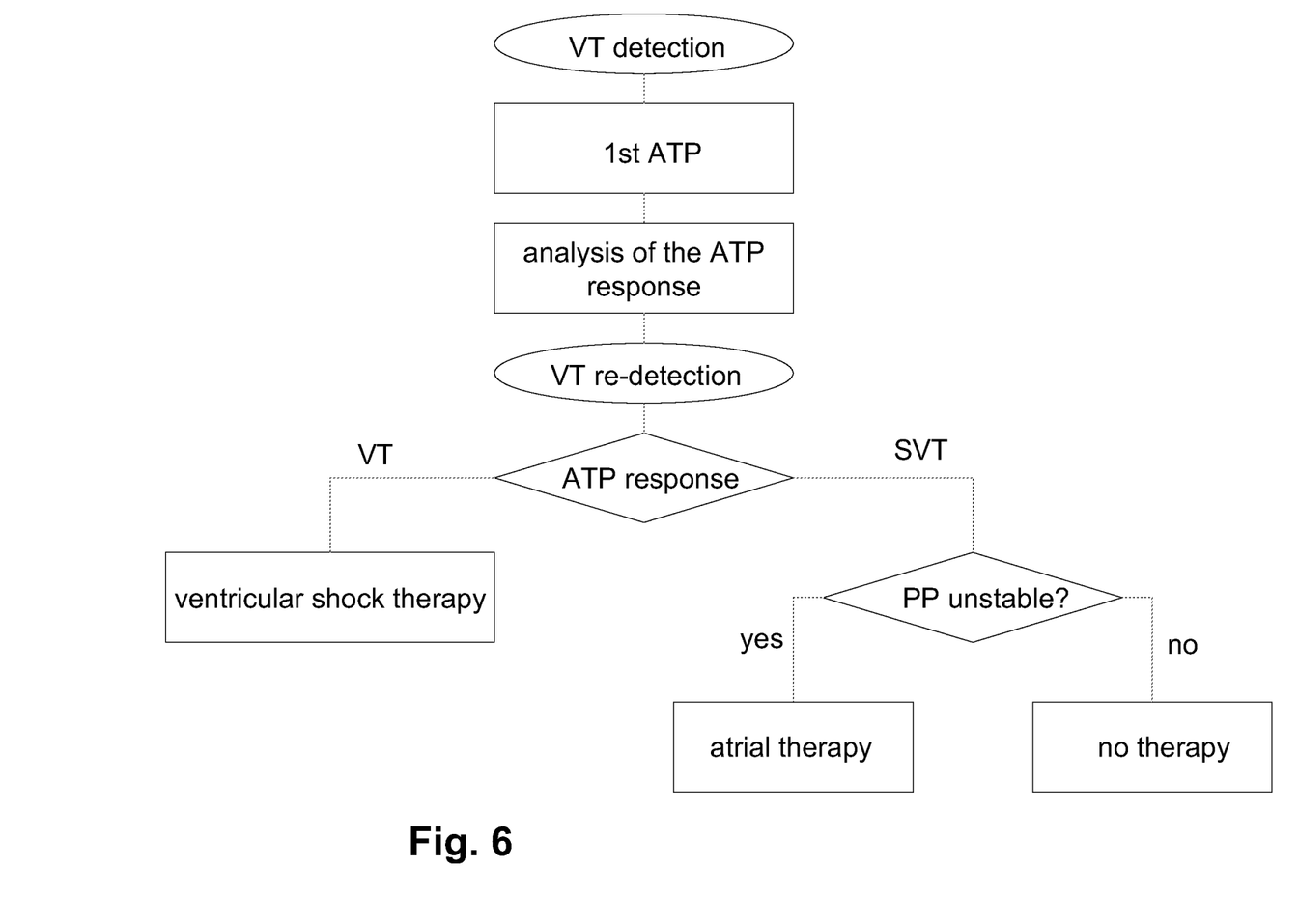
FIG. 6: shows a third implementation of a treatment control in response to an ATP response signal in the form of a flow chart.

FIG. 6 shows another variant of the implementation:

Unlike FIG. 4, in the case of an ATP response signal representing SVT, after re-detection a decision is made here as to whether the atrial arrhythmia is stable or unstable, and in the event of an atrial fibrillation (unstable), an atrial treatment (HF burst or cardioversion shock) is initiated. However, if the atrial rhythm is stable, there is no delivery of treatment (exercise-induced increase in frequency).

What is claimed is:

1. An implantable cardiac stimulator, comprising
a chamber stimulation unit (56; 64), which is connected or connectable to a left ventricular or right ventricular stimulation electrode to generate and deliver chamber stimulation pulses for stimulation of a ventricle of a heart;
a ventricular sensing unit (58; 66), which is configured to detect a respective chamber contraction and to deliver a ventricular sensing signal when a chamber contraction is detected;
an atrial sensing unit (62), which is configured to detect an atrial contraction and to deliver an atrial sensing signal that indicates a respective atrial event when the atrial contraction is detected;
a tachycardia detection unit (170), which is connected to at least one ventricular sensing unit comprising said ventricular sensing unit and is configured to detect a tachycardia and to categorize the tachycardia as a ventricular tachycardia VT or as a supraventricular tachycardia SVT;
a treatment control unit (190), which is configured to trigger at least the chamber stimulation unit (56; 64) to deliver antitachycardiac stimulation ATP; and,
an analyzer unit (200), which is connected to the atrial sensing unit (62) and to the treatment control unit wherein the analyzer unit is configured to analyze atrial events detected by the atrial sensing unit (62) before, during and after delivery of the antitachycardiac stimulation ATP with regard to an atrial rhythm pattern during ventricular ATP by comparison with the atrial rhythm pattern immediately before ATP and to trigger the treatment control unit (190) as a function of an ATP response signal that represents a result of the comparison for selection of a following antitachycardiac treatment.

2. The implantable cardiac stimulator according to claim 1, wherein the analyzer unit (200) is configured to generate the ATP response signal that indicates the supraventricular tachycardia SVT when the comparison of the atrial rhythm pattern reveals that an atrial rhythm remains uninfluenced by the ventricular ATP.

3. The implantable cardiac stimulator according to claim 1, wherein the analyzer unit (200) is configured to confirm the ventricular tachycardia VT and to generate the ATP response signal that indicates the ventricular tachycardia VT when the comparison of the atrial rhythm pattern reveals that an atrial rhythm is modulated by the ventricular ATP.

4. The implantable cardiac stimulator according to claim 1, wherein the ventricular sensing unit (58; 66) is connected or connectable to a left ventricular or right ventricular sensing electrode and is configured to detect electric potentials of a respective heart chamber and analyze the electric potentials with respect to the chamber contraction.

5. The implantable cardiac stimulator according to claim 1, wherein the atrial sensing unit (62) is connected or connectable to an atrial sensing electrode and is configured to detect electric potentials of an atrium or a right atrium of the heart.

6. The implantable cardiac stimulator according to claim 1, wherein the tachycardia detection unit (170) is configured to assign a current ventricular rhythm to at least one VT zone and one VF zone.

7. The implantable cardiac stimulator according to claim 1, further comprising a defibrillation shock generator (50), which is connected or connectable to a defibrillation shock electrode (38) and is configured to generate and deliver a defibrillation shock for defibrillation of at least one chamber.

8. The implantable cardiac stimulator according to claim 7, wherein the treatment control unit (190) is configured to inhibit delivery of the defibrillation shock when the ATP response signal indicates occurrence of the supraventricular tachycardia SVT.

9. The implantable cardiac stimulator according to claim 7, wherein the treatment control unit (190) is configured to inhibit delivery of a defibrillation shock when the ATP response signal indicates occurrence of the supraventricular tachycardia SVT and a respective ventricular heart rate is in the at least one VT zone.

10. The implantable cardiac stimulator according to claim 1, wherein the analyzer unit (200) is configured to analyze an atrial rhythm immediately after the antitachycardiac stimulation ATP compared with the atrial rhythm immediately before the antitachycardiac stimulation ATP.

11. The implantable cardiac stimulator according to claim 1, wherein the treatment control unit (190) is configured to inhibit a subsequent antitachycardiac treatment with the function of the ATP response signal.

12. The implantable cardiac stimulator according to claim 1, wherein the treatment control unit (190) is configured to continue a subsequent antitachycardiac treatment with the function of the ATP response signal.

13. The implantable cardiac stimulator according to claim 1, wherein the treatment control unit (190) is configured to replace a subsequent antitachycardiac ventricular therapy with the function of the ATP response signal by an atrial antitachycardiac therapy.

14. The implantable cardiac stimulator according to claim 1, wherein the treatment control unit (190) is configured to first start a new VT/SVT classification with the function of the ATP response signal.

15. The implantable cardiac stimulator according to claim 1, wherein the treatment control unit (190) is configured to adapt a subsequent antitachycardiac treatment with the function of the ATP response signal based on parameters of a ventricular antitachycardiac therapy.

* * * * *